US00PP27645P3

(12) United States Plant Patent
Vitten et al.

(10) Patent No.: US PP27,645 P3
(45) Date of Patent: Feb. 7, 2017

(54) STRAWBERRY PLANT NAMED 'DRISSTRAWFORTYFIVE'

(50) Latin Name: *Fragaria×ananassa*
Varietal Denomination: DrisStrawFortyFive

(71) Applicant: DRISCOLL STRAWBERRY ASSOCIATES, INC., Watsonville, CA (US)

(72) Inventors: Matthias D. Vitten, Aptos, CA (US); Carlos D. Fear, West Malling (GB); Katalin Pakozdi, Maidstone (GB)

(73) Assignee: Driscoll's, Inc., Watsonville, CA (US)

( * ) Notice: Subject to any disclaimer, the term of this patent is extended or adjusted under 35 U.S.C. 154(b) by 83 days.

(21) Appl. No.: 14/544,902

(22) Filed: Mar. 6, 2015

(65) Prior Publication Data

US 2016/0270276 P1 Sep. 15, 2016

(51) Int. Cl.
*A01H 5/08* (2006.01)

(52) U.S. Cl.
USPC ..... Plt./208

(58) Field of Classification Search
USPC ..... Plt./208
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson, Jr.
PP5,480 P 5/1985 Nakagawa
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,889 P2 8/2002 Lamb et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 Lopez
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.
PP20,248 P3 9/2009 Rogers et al.
PP20,701 P2 2/2010 Gilford et al.
PP20,731 P2 2/2010 Mowrey et al.

(Continued)

OTHER PUBLICATIONS

Vitten et al, U.S. Appl. No. 14/545,234, filed Apr. 10, 2015 titled "Strawberry Plant Named Drisstrawfortysix".
Kibbe et al, U.S. Appl. No. 14/545,991, filed Jul. 15, 2015, titled "Strawberry Plant Named Drisstrawfortynine".
Ferguson et al, U.S. Appl. No. 14/545,992, filed Jul. 15, 2015. titled "Strawberry Plant Named Drisstrawfortyseven".
Kibbe et al, U.S. Appl. No. 14/756,125, filed Aug. 4, 2015, titled "Strawberry Plant Named Drisstrawfortyeight".
Vitten et al, U.S. Appl. No. 14/999,062, filed Mar. 25, 2016 titled "Strawberry Plant Named Drisstrawfifty".

*Primary Examiner* — Anne Grunberg
(74) *Attorney, Agent, or Firm* — Morrison & Foerster LLP

(57) ABSTRACT

A new and distinct variety of strawberry plant named 'DrisStrawFortyFive' particularly characterized by medium red, sweet fruit, early harvest maturity and moderate resistance to powdery mildew, is disclosed.

2 Drawing Sheets

(56) References Cited

U.S. PATENT DOCUMENTS

| | | | |
|---|---|---|---|
| PP20,733 | P2 | 2/2010 | Mowrey et al. |
| PP20,735 | P2 | 2/2010 | Ferguson |
| PP20,775 | P2 | 2/2010 | Mowrey et al. |
| PP20,922 | P2 | 4/2010 | Gilford et al. |
| PP21,538 | P2 | 11/2010 | Gilford et al. |
| PP21,559 | P2 | 12/2010 | Ferguson et al. |
| PP21,762 | P2 | 3/2011 | Stewart et al. |
| PP22,040 | P3 | 7/2011 | Stewart et al. |
| PP22,218 | P2 | 11/2011 | Ferguson |
| PP22,247 | P2 | 11/2011 | Ferguson |
| PP23,107 | P2 | 10/2012 | Ferguson et al. |
| PP23,148 | P2 | 10/2012 | Gilford et al. |
| PP23,377 | P2 | 2/2013 | Ferguson et al. |
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| 2003/0079263 | P1 | 4/2003 | Gilford et al. |
| 2013/0276182 | P1 | 10/2013 | Fear et al. |

Genus and species: *Fragaria×ananassa.*

Variety denomination: 'DrisStrawFortyFive'.

BACKGROUND OF THE NEW PLANT

The present invention relates to a new and distinct strawberry variety designated 'DrisStrawFortyFive' and botanically known as *Fragaria×ananassa*. This new strawberry variety was discovered in Kent, United Kingdom in June 2010 and originated from a cross between the proprietary female parent 'QUK 214-001' (unpatented) and the proprietary male parent 'KGEM 0629-001' (unpatented). A single plant was selected and asexually propagated via tissue culture and vegetative cuttings in Kent, United Kingdom in 2010.

'DrisStrawFortyFive' underwent further testing in Kent, United Kingdom from 2010-2014. The present invention has been found to retain its distinctive characteristics through successive asexual propagations via stolons and tissue culture.

SUMMARY OF THE INVENTION

The following are the most outstanding and distinguishing characteristics of this new cultivar when grown under normal horticultural practices in Kent, United Kingdom.

1. Medium red, sweet fruit;
2. Early harvest maturity; and
3. Moderate resistance to powdery mildew.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from ten to twelve-month-old plants.

DESCRIPTION OF THE NEW VARIETY

Figure 1:
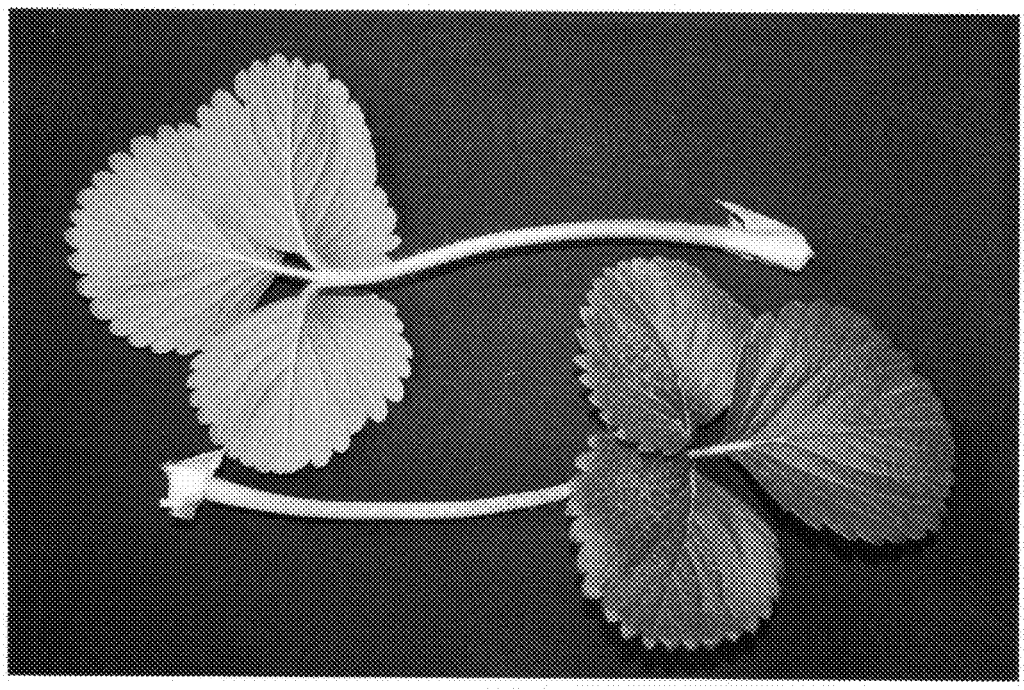
FIG. 1 shows upper and lower surfaces of the leaves of the plant with three leaflets.
Figure 2:
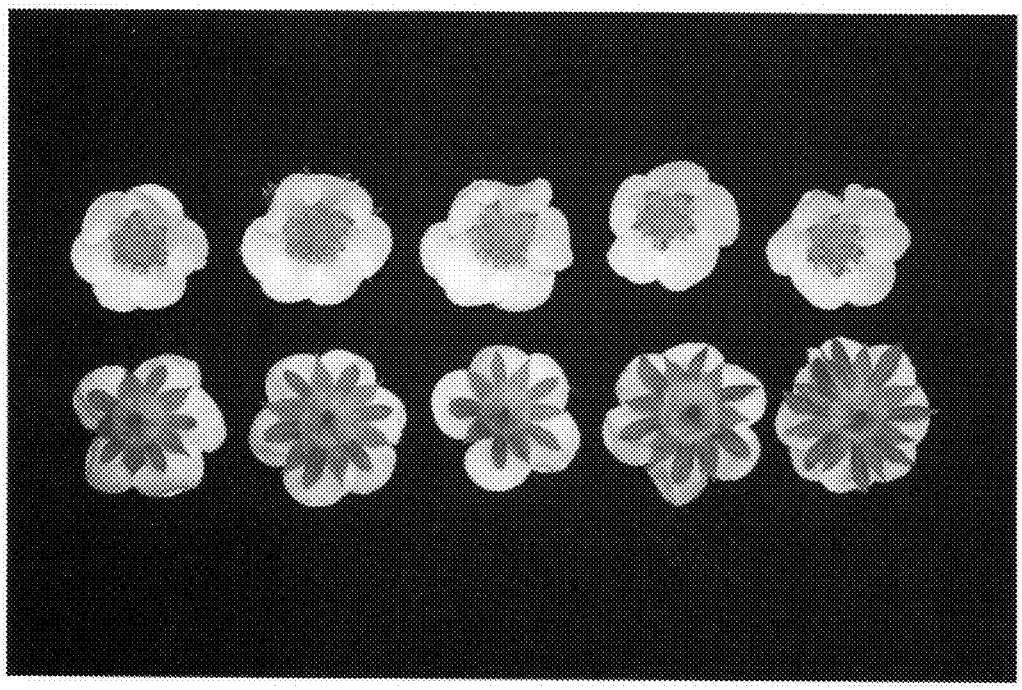
FIG. 2 shows both upper and lower surfaces of the flowers.
Figure 3:
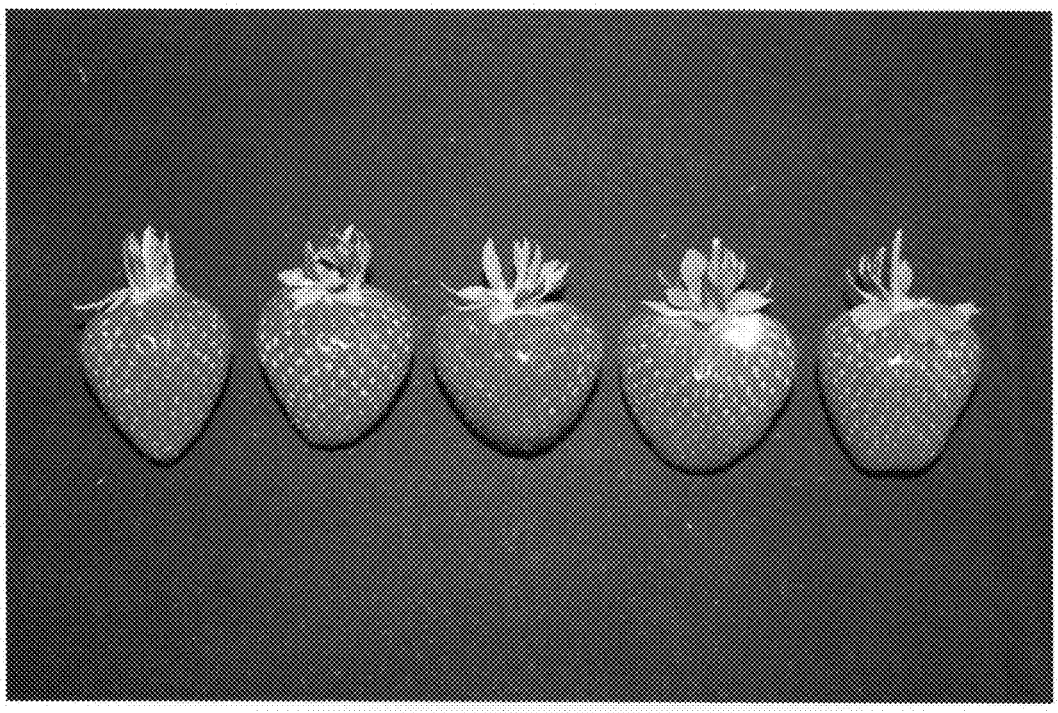
FIG. 3 shows the whole fruit.
Figure 4:
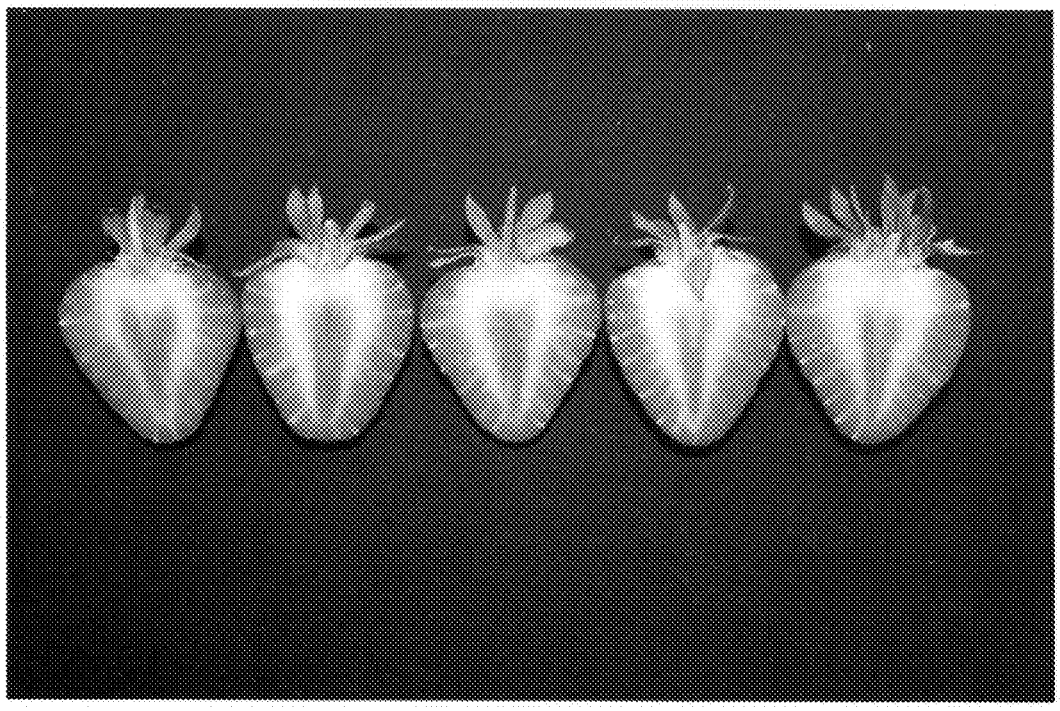
FIG. 4 shows the fruit in longitudinal cross-section.

The following detailed descriptions set forth the distinctive characteristics of 'DrisStrawFortyFive'. The data which define these characteristics is based on observations taken in Kent, United Kingdom from 2010 to 2014. This description is in accordance with UPOV terminology. Color designations, color descriptions, and other phenotypical descriptions may deviate from the stated values and descriptions depending upon variation in environmental, seasonal, climatic, and cultural conditions. 'DrisStrawFortyFive' has not been observed under all possible environmental conditions. The botanical description of 'DrisStrawFortyFive' was taken from ten to twelve-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION OF THE PLANT

Classification:
- *Species.*—*Fragaria×ananassa.*
- *Common name.*—Strawberry.
- *Denomination.*—'DrisStrawFortyFive'.

Parentage:
- *Female parent.*—The proprietary variety 'QUK 214-001' (unpatented).
- *Male parent.*—The proprietary variety 'KGEM 0629-001' (unpatented).

Plant:
- *Height.*—47.1 cm.
- *Diameter.*—56.7 cm.
- *Number of crowns/plant.*—4.
- *Habit.*—Upright.
- *Density of individual plant.*—Medium.
- *Vigor* (*health and hardiness of plant*).—Medium.

Terminal leaflets:
- *Size.*—Medium. Length: 10.8 cm. Width: 9.9 cm. Length/width ratio: 1.1 (Longer than broad).
- *Number of teeth/terminal leaflet.*—20.
- *Shape of teeth.*—Obtuse — serrate to crenate.
- *Color.*—Upper surface: RHS N137C (Dark green). Lower surface: RHS 137C (Medium green).
- *Shape in cross section.*—Slightly concave.
- *Blistering.*—Weak.
- *Glossiness.*—Medium.
- *Number of leaflets.*—Three only.
- *Shape.*—Orbicular.
- *Base shape.*—Obtuse.
- *Apex descriptor.*—Convex.
- *Margin.*—Serrate.
- *Margin profile.*—Revolute (margins rolled backwards).
- *Variegation.*—Absent.

Petiole:
- *Length.*—Medium; 32.9 cm.
- *Diameter.*—8.31 mm.
- *Pubescence.*—Medium.
- *Pose of hairs.*—Slightly upwards.
- *Color.*—RHS 144B (Medium yellow-green).
- *Bract frequency.*—0.

Petiolule:
- *Length.*—8.31 mm.
- *Diameter.*—2.94 mm.
- *Color.*—RHS N144C (Medium yellow-green).

Stipule:
- *Length.*—39.4 mm.
- *Width.*—11.13 mm.
- *Pubescence.*—Medium.
- *Stipule anthocyanin coloration.*—Weak; RHS 63C (Medium red-purple).

Stolons:
- *Number of stolons.*—Many.
- *Average number of daughter plants* (*per square meter*).—114.
- *Anthocyanin coloration.*—Absent or very weak; RHS 144C (Medium yellow-green).
- *Diameter at bract.*—3.31 mm.
- *Thickness.*—Thick.
- *Density of pubescence.*—Sparse.

Inflorescence:
- *Position relative to foliage.*—Level.
- *Number of flowers per plant.*—Many.
- *Time of flowering* (50% *of plants at first flower*).—Late April-early June.

*Flower size*.—Medium.

*Flower diameter*.—29.44 mm.

*Petals*.—Shape: Orbicular. Apex: Rounded. Base: Concavo-convex. Margin: Entire. Spacing: Overlapping. Length: 12.93 mm. Width: 14.20 mm. Length/width ratio: 0.9 (Broader than long). Petal number per flower: 5. Color (upper surface): RHS NN155C (White).

*Calyx*.—Diameter: 26.65 mm. Diameter relative to corolla: Smaller. Inner calyx diameter relative to outer: Same size. Insertion of calyx: Level. Pose of calyx segments: Spreading — outwards. Size of calyx in relation to fruit: Slightly smaller. Adherence of calyx: Medium.

*Sepal*.—Shape: Ovate. Apex: Acuminate. Margin: Entire. Length: 9.11 mm. Width: 4.99 mm. Sepal number: 10-12.

*Receptacle color*.—RHS 12B (Medium yellow).

*Stamen*.—Present. Anther color: RHS 153C (Medium yellow-green).

*Pedicel*.—Attitude of hairs: Slightly upwards.

Fruiting truss:

*Length*.—Long; 42.4 cm.

*Diameter at base of truss*.—5.98 mm.

*Number of berries per fruiting truss*.—11.

*Attitude at first picking*.—Semi-erect.

*Color at base of truss*.—RHS 144B (Medium yellow-green).

Fruit:

*Relative fruit size*.—Medium.

*Length*.—41.54 mm.

*Width*.—40.15 mm.

*Length/width ratio*.—1.0 (As long as broad).

*Fruit hollow length*.—30.47 mm.

*Fruit hollow width*.—15.42 mm.

*Fruit hollow length/width ratio*.—2.0 (Longer than broad).

*Fruit hollow center* (*cavity*).—Medium.

*Fruit weight*.—23.0 g.

*Predominant fruit shape*.—Conical.

*Difference in shape between primary and secondary fruits*.—None or very slight.

*Evenness of fruit surface*.—Even or very slightly uneven.

*Fruit skin color*.—RHS 42B (Medium red).

*Evenness of fruit color*.—Even or very slightly uneven.

*Fruit glossiness*.—Medium.

*Achenes*.—Insertion of achenes: Below surface. Coloration (sunward side of berry): RHS N167A (Medium greyed-orange). Coloration (shaded side of berry): RHS N167C (Medium greyed-orange). Number per berry: 262. Weight (weight of achenes divided by total # seed): 0.0086 g. Width of band without achenes: Absent or very narrow.

*Firmness of flesh* (*when fully ripe*).—Medium.

*Color of flesh* (*excluding core*).—RHS 40B (Medium red).

*Color of core*.—RHS 40C (Medium red).

*Evenness of flesh color*.—Even.

*Distribution of flesh color*.—Marginal and central.

*Sweetness*.—9.4 degree Brix.

*Texture when tasted*.—Fine.

*Type of bearing*.—Not everbearing — not remontant.

*Harvest interval*.—Late May-mid-July.

*Harvest maturity*.—Early.

*Production*.—870 grams per plant in Class I & II UK (2012-2014).

Disease and pest resistance:

*Powdery mildew*.—Moderately resistant.

*Verticillium wilt*.—Moderately susceptible.

COMPARISON WITH PARENTAL AND COMMERCIAL VARIETIES

When 'DrisStrawFortyFive' is compared to the female parent 'QUK 214-001' (unpatented), 'DrisStrawFortyFive' is higher yielding, lighter red color, and better flavor with similar fruit size and shelf life than 'QUK 214-001'.

When 'DrisStrawFortyFive' is compared to the male parent 'KGEM 0629-001' (unpatented), 'DrisStrawFortyFive' has fruit that is lighter red color and slightly larger in size than 'KGEM 0629-001'.

'DrisStrawFortyFive' differs from the commercial variety 'Sonata' (U.S. Plant Pat. No. 18,000), in that 'DrisStrawFortyFive' has orbicular shaped petals having a concavo-convex base, whereas 'Sonata' has broadly ovate shaped petals having an attenuate base. Additionally, 'DrisStrawFortyFive' has a medium-sized fruit hollow center and achenes that are inserted below the fruit surface, whereas 'Sonata' has an absent or weakly expressed fruit hollow center and achenes that are inserted level with the fruit surface.

'DrisStrawFortyFive' differs from the commercial variety 'Elsanta' (unpatented), in that 'DrisStrawFortyFive' has medium-sized fruit with medium flesh firmness and a medium red colored core, whereas 'Elsanta' has large, firm fruit with a white colored core.

We claim:

1. A new and distinct variety of strawberry plant named 'DrisStrawFortyFive', substantially as illustrated and described herein.

* * * * *